(12) United States Patent
Watanabe et al.

(10) Patent No.: US 9,658,270 B2
(45) Date of Patent: May 23, 2017

(54) INSPECTION METHOD OF SENSOR DEVICE AND SENSOR DEVICE

(71) Applicant: ALPS ELECTRIC CO., LTD., Tokyo (JP)

(72) Inventors: Takuya Watanabe, Miyagi-ken (JP); Shuji Yanagi, Miyagi-ken (JP); Shinya Yokoyama, Miyagi-ken (JP); Toshiyuki Oki, Miyagi-ken (JP); Akira Asao, Miyagi-ken (JP)

(73) Assignee: ALPS ELECTRIC CO., LTD., Tokyo (JP)

( * ) Notice: Subject to any disclaimer, the term of this patent is extended or adjusted under 35 U.S.C. 154(b) by 244 days.

(21) Appl. No.: 14/634,495

(22) Filed: Feb. 27, 2015

(65) Prior Publication Data

US 2015/0253372 A1 Sep. 10, 2015

(30) Foreign Application Priority Data

Mar. 6, 2014 (JP) .................................. 2014-043953

(51) Int. Cl.
*G01R 31/04* (2006.01)
*G01N 27/22* (2006.01)
*G01R 27/26* (2006.01)
*G01R 31/02* (2006.01)
*H04L 1/00* (2006.01)

(52) U.S. Cl.
CPC ......... *G01R 31/041* (2013.01); *G01N 27/223* (2013.01); *G01R 27/2605* (2013.01); *G01R 31/024* (2013.01); *G01N 27/228* (2013.01); *H01L 2221/00* (2013.01); *H04L 1/00* (2013.01); *H04L 2201/00* (2013.01)

(58) Field of Classification Search
CPC ....... H04L 1/00; H04L 2201/00; G06Q 10/00; H01L 21/00; H01L 2221/00; G06F 1/00; G06F 2101/00
See application file for complete search history.

(56) References Cited

U.S. PATENT DOCUMENTS

| 2003/0052867 | A1* | 3/2003 | Shigetaka | ............... G06F 3/044 |
| | | | | 345/173 |
| 2004/0193988 | A1 | 9/2004 | Saloio | |
| 2006/0119369 | A1* | 6/2006 | Kawahata | ............ G06K 9/0002 |
| | | | | 324/662 |
| 2006/0158202 | A1* | 7/2006 | Umeda | ................ G06K 9/0002 |
| | | | | 324/686 |

(Continued)

*Primary Examiner* — Jermele M Hollington
*Assistant Examiner* — Temilade Rhodes-Vivour
(74) *Attorney, Agent, or Firm* — Beyer Law Group LLP

(57) ABSTRACT

In a reset period of a first stage, a switching circuit is turned on, and high-level driving voltages are output from driving circuits. In a charge transfer period subsequent to the reset period, the switching circuit is turned off, and low-level driving voltages are output from the driving circuits. It is determined whether or not an output voltage of an amplifier circuit in the charge transfer period is included in a normal range. In the inspection of a second stage subsequent to the first stage, in the same manner as in the normal measurement, voltages having opposite phases are output from the driving circuits in the reset period and the charge transfer period, and it is determined whether or not the output voltage of the amplifier circuit in the charge transfer period is included in a normal range.

6 Claims, 15 Drawing Sheets

(56) References Cited

U.S. PATENT DOCUMENTS

2009/0012733 A1\* 1/2009 Yamada ................. G01C 17/38
  702/92
2012/0319677 A1\* 12/2012 Bogner .............. G01R 19/0092
  324/126

\* cited by examiner

SW1

DRV1

DRV2

Vo

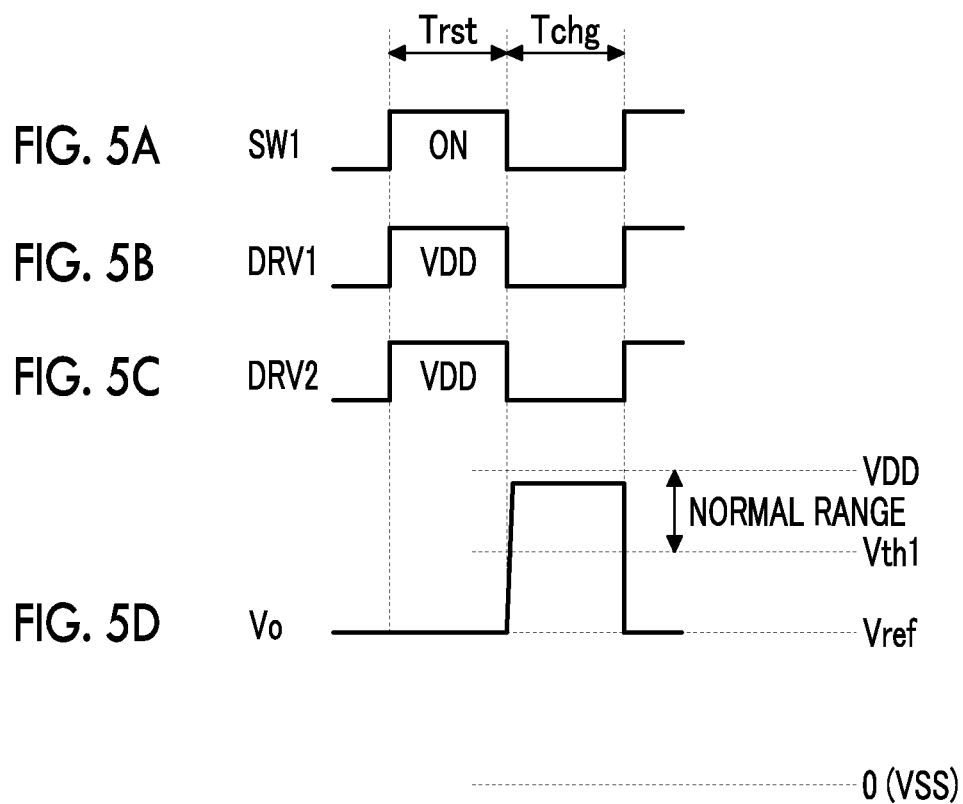

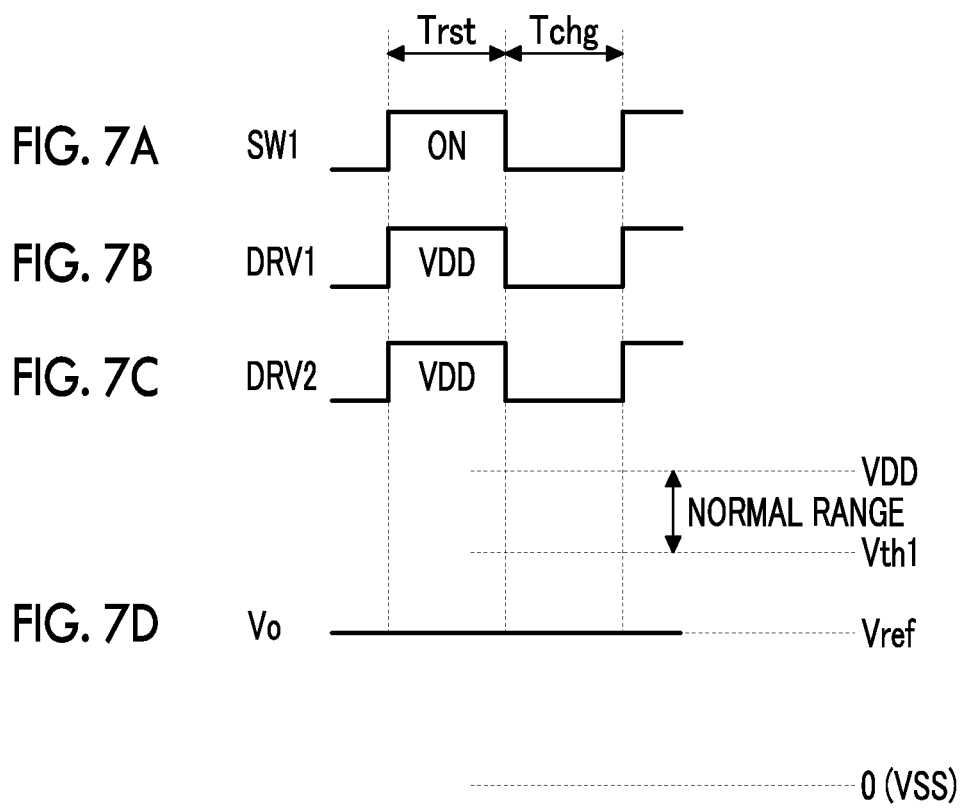

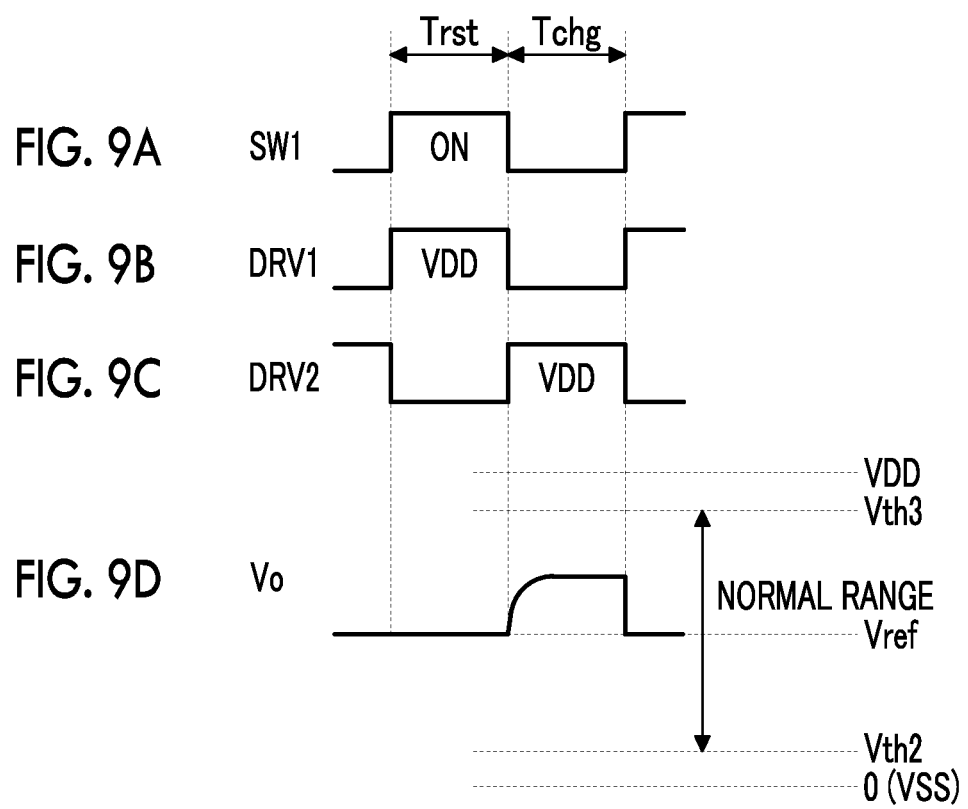

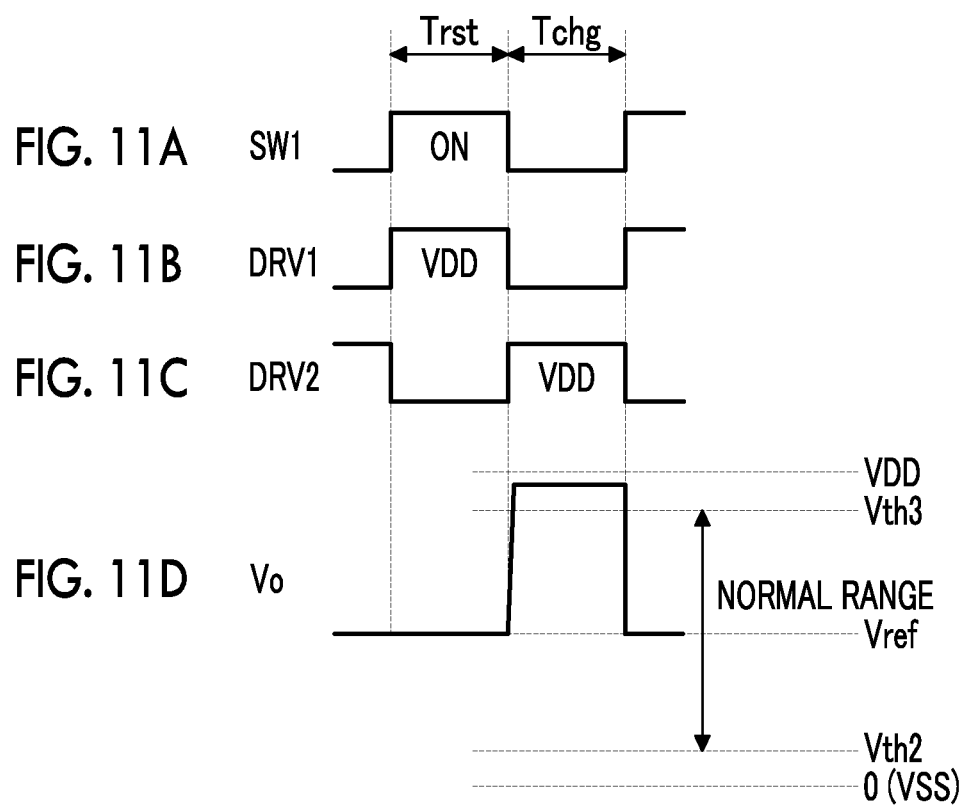

INSPECTION METHOD OF SENSOR DEVICE AND SENSOR DEVICE

CLAIM OF PRIORITY

This application claims benefit of Japanese Patent Application No. 2014-043953 filed on Mar. 6, 2014, which is hereby incorporated by reference.

BACKGROUND OF THE INVENTION

1. Field of the Invention

The present invention relates to an inspection method of a sensor device using a capacitive sensor element, and in particular, to an inspection method of a sensor device including a circuit for converting the capacitance of a capacitive sensor element into a voltage.

2. Description of the Related Art

As electric humidity sensors, a resistive humidity sensor using a sensor element having an electrical resistance that changes according to humidity and a capacitive humidity sensor using a sensor element having a capacitance that changes are generally known.

FIGS. 14A and 14B are diagrams showing the configuration of a resistive humidity sensor. A sensor unit 100 is a circuit including a sensor element having a resistance that changes according to humidity, and a DC voltage is applied to the sensor unit 100. When the resistance of the sensor element changes, the voltage of the signal line also changes according to the resistance change. An amplifier circuit 101 amplifies the voltage of the signal line, and outputs the amplified voltage as a humidity detection signal.

On the other hand, FIG. 15 is a diagram showing the configuration of a capacitive humidity sensor. A sensor unit 110 is a circuit including a sensor element having a capacitance that changes according to humidity, and an AC voltage is applied to both ends of the sensor unit 110. When the capacitance of the sensor element changes, electric charges according to the change are accumulated in a capacitor 114. An operational amplifier 113 outputs a voltage corresponding to the electric charges accumulated in the capacitor 114 as a humidity detection signal.

In the case of the resistive sensor using a sensor element having an electrical resistance that changes, as shown in FIGS. 14A and 14B, it is possible to make a constant current flow through the signal line using a constant current source 102. If the signal line is broken, the voltage of the signal line is reduced to the ground level by the current of the constant current source 102. Accordingly, the output voltage of the amplifier circuit 101 becomes an abnormal value. Thus, in the resistive humidity sensor, it is possible to inspect the breakage of the signal line relatively easily using the constant current source. However, in the case of the capacitive sensor using a sensor element having a capacitance that changes, as shown in FIG. 15, a circuit configuration for inputting electric charges corresponding to the capacitance to charge amplifiers 113, 114, and 115 and converting the electric charges into a voltage is common. When a constant current source is connected to the signal line for transferring the electric charges to the charge amplifier from the sensor unit, the charge amplifier integrates the current of the constant current source. Accordingly, electric charges corresponding to the capacitance of the sensor element cannot be detected successfully. That is, the capacitive sensor has a problem that the breakage of the signal line cannot be detected using the constant current source unlike the resistive sensor.

In addition, in the case of the capacitive sensor, as shown in FIG. 15, an AC voltage is applied to the sensor unit 110. For this reason, the sensor unit 110 and a driving circuit of AC voltage need to be connected to each other by wire bonding or the like. In this case, the wiring line may also be broken. When performing wire bonding, the wires may be short-circuited. Therefore, in the capacitive sensor, not only may the signal line be broken, but also the wiring lines of the driving circuit may be broken or may be short-circuited. It has been an issue to inspect these failures appropriately.

SUMMARY OF THE INVENTION

The present invention provides an inspection method of a sensor device capable of appropriately inspecting the breakage or short-circuiting of wiring lines connected to a capacitive sensor element and a sensor device that performs such an inspection.

According to a first aspect of the present invention, there is provided an inspection method of a sensor device. The sensor device includes: a sensor unit including a first capacitive sensor element connected between a first driving terminal and a signal terminal and a second capacitive sensor element connected between a second driving terminal and the signal terminal; a first driving circuit configured to output a first driving voltage or a second driving voltage to the first driving terminal; a second driving circuit configured to output the first driving voltage or the second driving voltage to the second driving terminal; a capacitor having an end connected to the signal terminal; an amplifier circuit configured to output a voltage, which is obtained by amplifying a difference between a voltage of the signal terminal and a reference voltage, to the other end of the capacitor so that the voltage of the signal terminal becomes close to the reference voltage; and a switching circuit configured to discharge electric charges accumulated in the capacitor. The inspection method of a sensor device according to the first aspect of the present invention includes: a first step of discharging the capacitor by using the switching circuit and outputting the first driving voltage from both of the first and second driving circuits; a second step of releasing the discharge of the capacitor by the switching circuit and outputting the second driving voltage from both of the first and second driving circuits; and a third step of determining whether or not a voltage output from the amplifier circuit in the second step is included in a first normal range. A first inspection stage includes the first step, the second step, and the third step.

According to the inspection method described above, in the first step of the first stage, the capacitor is discharged by the switching circuit, and the first driving voltage is output from both of the first and second driving circuits. In the second step subsequent to the first step, the discharge of the capacitor by the switching circuit is released, and the second driving voltage is output from both of the first and second driving circuits. Then, it is determined whether or not the output voltage of the amplifier circuit in the second step is included in the first normal range, and a determination result indicating an abnormal state is obtained when the output voltage of the amplifier circuit is not included in the first normal range.

Preferably, the inspection method further includes: a fourth step of discharging the capacitor by using the switching circuit and outputting the first driving voltage from the first driving circuit and the second driving voltage from the second driving circuit; a fifth step of releasing the discharge of the capacitor by the switching circuit and outputting the second driving voltage from the first driving circuit and the first driving voltage from the second driving circuit; and a sixth step of determining whether or not a voltage output from the amplifier circuit in the fifth step is included in a second normal range. A second inspection stage may include the fourth step, the fifth step, and the sixth step, and may be performed when it is determined that the output voltage of the amplifier circuit in the first inspection stage is included in the first normal range.

According to the inspection method described above, when it is determined that the output voltage of the amplifier circuit in the first stage is included in the first normal range, the capacitor is discharged by using the switching circuit and the first driving voltage is output from the first driving circuit and the second driving voltage is output from the second driving circuit in the fourth step of the second stage. In the fifth step subsequent to the fourth step, the discharge of the capacitor by the switching circuit is released, and the second driving voltage is output from the first driving circuit and the first driving voltage is output from the second driving circuit. Then, it is determined whether or not the output voltage of the amplifier circuit in the fifth step is included in the second normal range, and a determination result indicating an abnormal state is obtained when the output voltage of the amplifier circuit is not included in the second normal range.

Preferably, the sensor device includes an offset adjustment circuit configured to adjust an offset voltage of the amplifier circuit. In this case, in the first inspection stage, a function of adjusting the offset voltage by the offset adjustment circuit may be disabled. In the second inspection stage, the function of adjusting the offset voltage by the offset adjustment circuit may be enabled.

Therefore, an erroneous determination due to the function of adjusting the offset voltage in the first inspection stage is prevented.

According to a second aspect of the present invention, there is provided a sensor device including the sensor unit, the first driving circuit, the second driving circuit, the capacitor, the amplifier circuit, the switching circuit, and a control circuit. The control circuit controls the first driving circuit, the second driving circuit, and the switching circuit so that a voltage corresponding to a difference between a capacitance of the first capacitive sensor element and a capacitance of the second capacitive sensor element is output from the amplifier circuit. The control circuit executes the first step, the second step, and the third step, and the first inspection stage includes the first step, the second step, and the third step.

Preferably, the control circuit executes the fourth step, the fifth step, and the sixth step, and the second inspection stage includes the fourth step, the fifth step, and the sixth step.

Preferably, the sensor device according to the second aspect of the present invention includes the offset adjustment circuit. The control circuit may disable a function of adjusting the offset voltage by the offset adjustment circuit in the first inspection stage, and enable the function of adjusting the offset voltage by the offset adjustment circuit in the second inspection stage.

According to the aspects of the present invention, it is possible to convert the capacitance of the capacitive sensor element into continuous voltage.

BRIEF DESCRIPTION OF THE DRAWINGS

FIG. 2A shows the ON/OFF state of the switching circuit, FIG. 2B shows the driving voltage of a first driving circuit, FIG. 2C shows the driving voltage of a second driving circuit, and FIG. 2D shows the output voltage of an amplifier circuit;

FIG. 4A shows an operating state in a reset period of the first stage and FIG. 4B shows an operating state in a charge transfer period of the first stage;

FIGS. 5A to 5D are diagrams for explaining the state of the switching circuit and the voltage of each portion in the first stage of the inspection sequence and show a case where there is no breakage of the signal line, where FIG. 5A shows the ON/OFF state of the switching circuit, FIG. 5B shows the driving voltage of the first driving circuit, FIG. 5C shows the driving voltage of the second driving circuit, and FIG. 5D shows the output voltage of the amplifier circuit;

FIGS. 7A to 7D are diagrams for explaining the state of the switching circuit and the voltage of each portion in the first stage of the inspection sequence, and show a case where the signal line is broken, where FIG. 7A shows the ON/OFF state of the switching circuit, FIG. 7B shows the driving voltage of the first driving circuit, FIG. 7C shows the driving voltage of the second driving circuit, and FIG. 7D shows the output voltage of the amplifier circuit;

FIG. 8A shows an operating state in a reset period of the second stage and FIG. 8B shows an operating state in a charge transfer period of the second stage;

FIGS. 9A to 9D are diagrams for explaining the state of the switching circuit and the voltage of each portion in the second stage of the inspection sequence and show a normal case where there is no breakage or the like, where FIG. 9A shows the ON/OFF state of the switching circuit, FIG. 9B shows the driving voltage of the first driving circuit, FIG. 9C shows the driving voltage of the second driving circuit, and FIG. 9D shows the output voltage of the amplifier circuit;

FIGS. 11A to 11D are diagrams for explaining the state of the switching circuit and the voltage of each portion in the second stage of the inspection sequence and show a case where the wiring line of a driving circuit is broken, where FIG. 11A shows the ON/OFF state of the switching circuit, FIG. 11B shows the driving voltage of the first driving circuit, FIG. 11C shows the driving voltage of the second driving circuit, and FIG. 11D shows the output voltage of the amplifier circuit;

FIG. 12A shows a case where the wiring lines of the first and second driving circuits are short-circuited and FIG. 12B shows a case where the wiring line of the second driving circuit and the signal line are short-circuited;

FIG. 14A shows a normal state and FIG. 14B shows a state where the signal line is broken.

DESCRIPTION OF THE PREFERRED EMBODIMENTS

Figure 1:
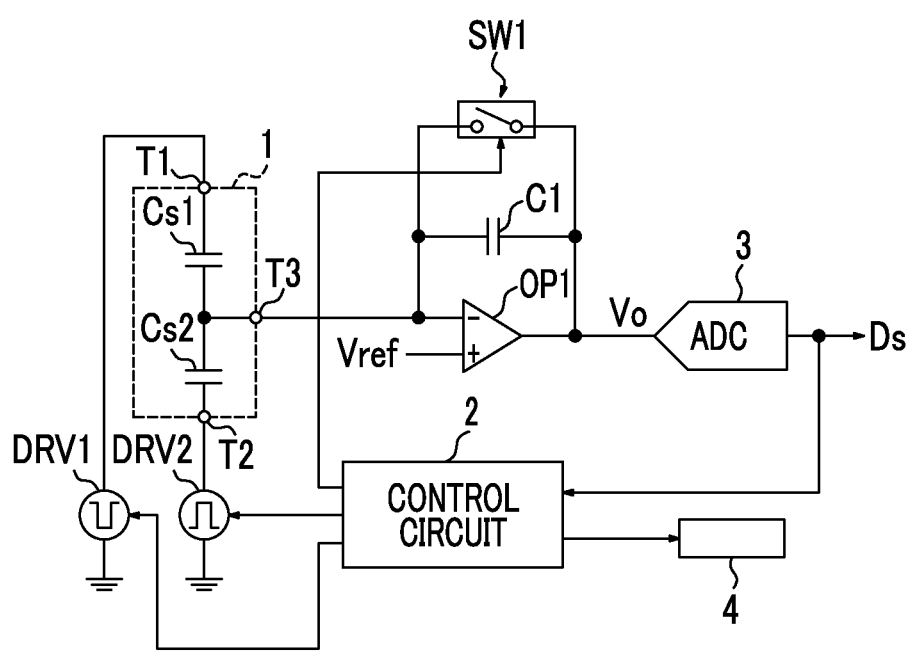
FIG. 1 is a diagram showing an example of the configuration of a sensor device according to an embodiment of the present invention.

FIG. 1 is a diagram showing an example of the configuration of a sensor device according to an embodiment of the present invention. The sensor device shown in FIG. 1 includes a sensor unit 1, a first driving circuit DRV1, a second driving circuit DRV2, a capacitor C1, an amplifier circuit OP1, a switching circuit SW1, a control circuit 2, an AD conversion circuit 3, and a register 4.

The sensor unit 1 is configured to include capacitive sensor elements Cs1 and Cs2 whose capacitance changes according to a physical quantity, such as humidity. The first capacitive sensor element Cs1 is connected between a first driving terminal T1 and a signal terminal T3, and the second capacitive sensor element Cs2 is connected between a second driving terminal T2 and the signal terminal T3. The first capacitive sensor element Cs1 and the second capacitive sensor element Cs2 are connected in series with each other at the signal terminal T3.

The first driving circuit DRV1 outputs a high-level driving voltage or a low-level driving voltage to the first driving terminal T1 of the sensor unit 1 under the control of the control circuit 2. The second driving circuit DRV2 outputs a high-level driving voltage or a low-level driving voltage to the second driving terminal T2 of the sensor unit 1 under the control of the control circuit 2. The high-level driving voltages output from the driving circuits are voltages approximately equal to a power supply voltage VDD, for example. The low-level driving voltages are voltages approximately equal to a ground potential VSS, for example.

One end of the capacitor C1 is connected to the signal terminal T3 of the sensor unit 1, and the other end is connected to the output of the amplifier circuit OP1. The amplifier circuit OP1 is, for example, an operational amplifier. The amplifier circuit OP1 outputs a voltage, which is obtained by amplifying a difference between the voltage of the signal terminal T3 and a reference voltage Vref, to the other end of the capacitor C1 so that the voltage of the signal terminal T3 becomes close to the reference voltage Vref. The voltage of the signal terminal T3 is input to the inverting input terminal of the amplifier circuit OP1, and the reference voltage Vref is input to the non-inverting input terminal. For example, the reference voltage Vref is set to an intermediate value between the high-level driving voltage and the low-level driving voltage output from the driving circuits DRV1 and DRV2. Since the voltage gain of the amplifier circuit OP1 is very large, the voltage of the signal terminal T3 is approximately equal to the reference voltage Vref. In addition, since the input impedance of the inverting input terminal of the amplifier circuit OP1 connected to the signal terminal T3 is very high, almost no current flows through the inverting input terminal.

The switching circuit SW1 is a circuit for discharging the electric charges accumulated in the capacitor C1, and is connected in parallel with the capacitor C1. The switching circuit SW1 is turned on or turned off under the control of the control circuit 2.

The AD conversion circuit 3 converts an output voltage Vo of the amplifier circuit OP1 into a digital signal. The AD conversion circuit 3 performs an analog-to-digital conversion operation under the control of the control circuit 2.

The control circuit 2 is a circuit for controlling the overall operation of the sensor device. For example, the control circuit 2 is formed by a dedicated logic circuit or CPU. That is, the control circuit 2 performs the generation of a driving voltage in the first driving circuit DRV1 or the second driving circuit DRV2, discharge of the capacitor C1 in the switching circuit SW1, and analog-to-digital conversion operation in the AD conversion circuit 3 based on a predetermined measurement sequence, and generates detection data Ds corresponding to the capacitance of the sensor unit 1. In addition, the control circuit 2 executes a predetermined inspection sequence for inspecting the breakage or short-circuiting of wiring lines in response to a command that is given from an external host device through a communication unit (not shown). When an inspection result of the inspection sequence that has been executed is obtained, the control circuit 2 writes the determination value (determination value indicating "normal" or "abnormal") of the inspection result in the register 4.

Figure 2A:
FIGS. 2A to 2D are diagrams for explaining the state of a switching circuit and the voltage of each portion in a normal measurement sequence for detecting the capacitance of a sensor unit 1 in the sensor device shown in FIG. 1, where
Figure 2B:
Figure 2C:
Figure 2D:
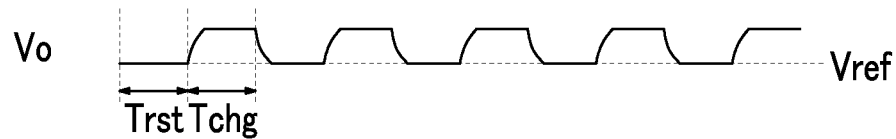

FIGS. 2A to 2D are diagrams for explaining the state of the switching circuit SW1 and the voltage of each portion in a normal measurement sequence for detecting the capacitance of the sensor unit 1 in the sensor device shown in FIG. 1. FIG. 2A shows the ON/OFF state of the switching circuit SW1, FIG. 2B shows the driving voltage of the first driving circuit DRV1, FIG. 2C shows the driving voltage of the second driving circuit DRV2, and FIG. 2D shows the output voltage Vo of the amplifier circuit OP1.

In the normal measurement sequence, the control circuit 2 repeats a reset period Trst and a charge transfer period Tchg alternately. In the reset period Trst, the control circuit 2 turns on the switching circuit SW1 to discharge the electric charges of the capacitor C1, and outputs the high-level driving voltage VDD from the first driving circuit DRV1 and outputs the low-level driving voltage VSS from the second driving circuit DRV2. In the charge transfer period Tchg, the control circuit 2 turns off the switching circuit SW1 so that the capacitor C1 can be charged, and outputs the low-level driving voltage VSS from the first driving circuit DRV1 and outputs the high-level driving voltage VDD from the second driving circuit DRV2.

Here, it is assumed that the capacitance of the first capacitive sensor element Cs1 is expressed as "Cs1" and the capacitance of the second capacitive sensor element Cs2 is expressed as "Cs2". In the reset period Trst, electric charges "−(VDD−Vref)×Cs1" are accumulated in the electrode of the first capacitive sensor element Cs1 connected to the signal terminal T3, and electric charges "Vref×Cs2" are accumulated in the electrode of the second capacitive sensor element Cs2 connected to the signal terminal T3. A total electric charge Q1 of the above is expressed by the following equation.

$$Q1 = -(VDD - Vref) \times Cs1 + Vref \times Cs2 \qquad (1)$$

In the charge transfer period Tchg, electric charges "Vref×Cs1" are accumulated in the electrode of the first capacitive sensor element Cs1 connected to the signal terminal T3, electric charges "−(VDD−Vref)×Cs2" are accumulated in the electrode of the second capacitive sensor element Cs2 connected to the signal terminal T3, and electric charges "−Vc1×C1" are accumulated in the electrode of the capacitor C1 connected to the signal terminal T3. Here, "Vc1" indicates a voltage of the capacitor C1 with respect to the electrical potential of the signal terminal T3 as a reference, and "C1" indicates the capacitance of the capacitor C1. A total electric charge Q2 of the above is expressed by the following equation.

$$Q2 = -(VDD - Vref) \times Cs2 + Vref \times Cs1 - Vc1 \times C1 \quad (2)$$

The input impedance of the inverting input terminal of the amplifier circuit OP1 is very high, and no electric charge is supplied to the node of the signal terminal T3 from the outside in the charge transfer period Tchg. Accordingly, the electric charge Q2 is equal to the electric charge Q1. Therefore, the voltage Vc1 of the capacitor C1 is expressed by the following equation from the equations (1) and (2).

$$Vc1 = VDD \times (Cs1 - Cs2)/C1 \quad (3)$$

Since the voltage of the signal terminal T3 is approximately equal to the reference voltage Vref, the output voltage Vo is expressed by the following equation.

$$Vo = VDD \times (Cs1 - Cs2)/C1 + Vref \quad (4)$$

As shown in equation (4), the voltage Vo output from the amplifier circuit OP1 in the normal measurement sequence is proportional to a difference Cs1−Cs2 between the capacitance of the first capacitive sensor element Cs1 and the capacitance of the second capacitive sensor element Cs2.

Figure 3:
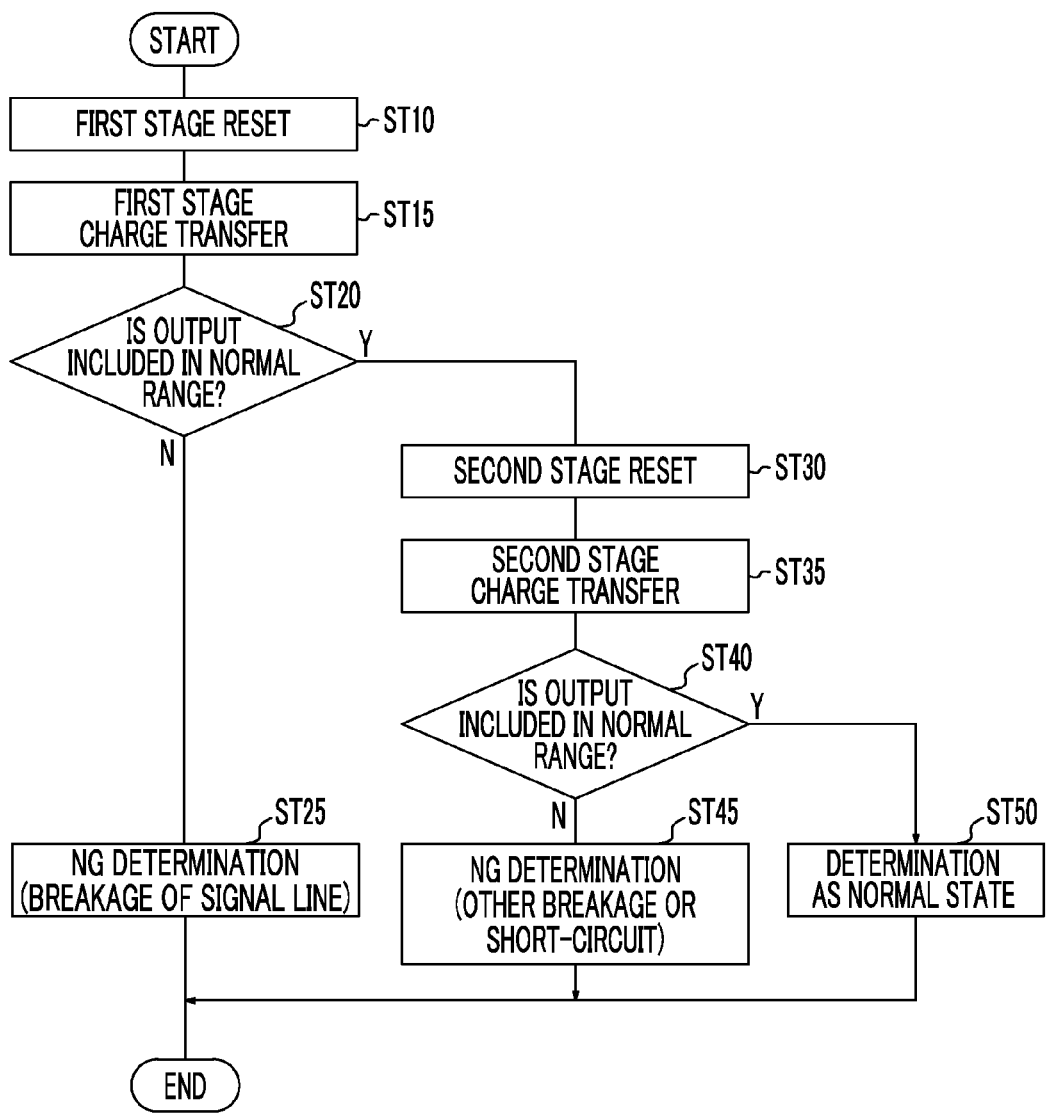
FIG. 3 is a flow chart for explaining the inspection sequence according to the present embodiment.

Next, a sequence for inspecting the breakage or the like in the sensor device will be described. FIG. 3 is a flow chart for explaining the inspection sequence according to the present embodiment. In the present embodiment, inspection is performed in two stages. In the first stage, driving voltages having the same phase are output from the first driving circuit DRV1 and the second driving circuit DRV2 (ST10, ST15), and breakage in the signal line between the signal terminal T3 and the capacitor C1 is mainly checked (ST20). In the second stage, driving voltages having opposite phases are output from the first driving circuit DRV1 and the second driving circuit DRV2 (ST30, ST35), and breakage or short-circuiting of wiring lines connected to the driving circuits DRV1 and DRV2 is mainly checked (ST40). First stage (ST10, ST15, ST20)

Figure 4A:
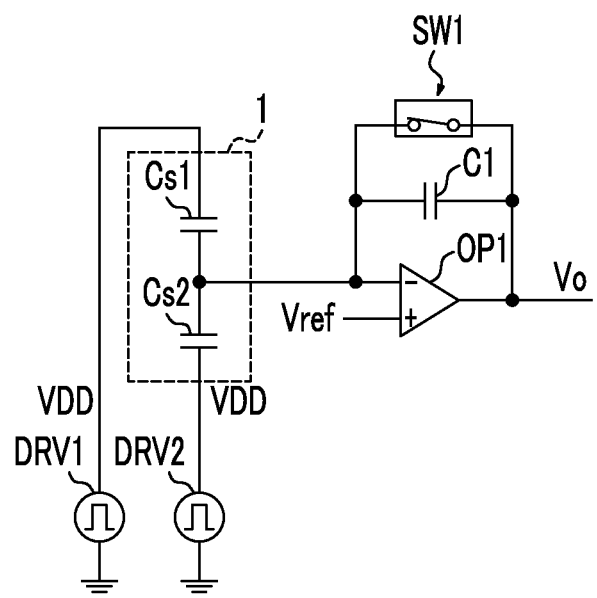
FIGS. 4A and 4B are diagrams showing the operating state of the sensor device in a first stage of the inspection sequence, where

In the reset period Trst of the first stage, the control circuit 2 turns on the switching circuit SW1 to discharge the electric charges of the capacitor C1, and outputs the high-level driving voltage VDD from both of the first driving circuit DRV1 and the second driving circuit DRV2 (ST10). FIG. 4A shows the operating state of the sensor device in the reset period Trst of the first stage. Since the high-level driving voltage VDD is higher than the reference voltage Vref, negative electric charges are accumulated in each electrode of the capacitive sensor elements Cs1 and Cs2 connected to the signal terminal T3. A total electric charge Q3 accumulated in the two capacitive sensor elements Cs1 and Cs2 in the reset period Trst is expressed by the following equation.

$$Q3 = -(VDD - Vref) \times (Cs1 + Cs2) \quad (5)$$

Figure 4B:
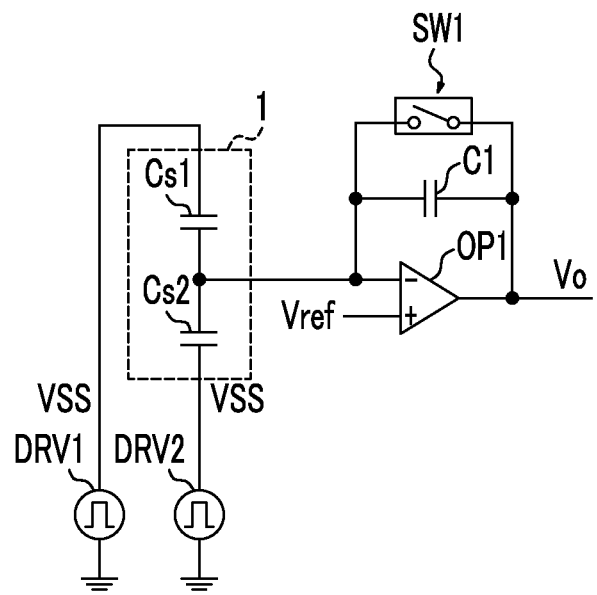

Then, in the charge transfer period Tchg of the first stage, the control circuit 2 turns off the switching circuit SW1 so that the capacitor C1 can be charged (discharge of the capacitor C1 is released), and outputs the low-level driving voltage VSS from both of the first driving circuit DRV1 and the second driving circuit DRV2 (ST15). FIG. 4B shows the operating state of the sensor device in the charge transfer period Tchg of the first stage. Since the low-level driving voltage VSS is lower than the reference voltage Vref, positive electric charges are accumulated in each electrode of the capacitive sensor elements Cs1 and Cs2 connected to the signal terminal T3. A total electric charge Q4 accumulated in the two capacitive sensor elements Cs1 and Cs2 and the capacitor C1 in the charge transfer period Tchg is expressed by the following equation.

$$Q4 = Vref \times (Cs1 + Cs2) - Vc1 \times C1 \quad (6)$$

Since the electric charge Q3 and the electric charge Q4 are equal, the voltage Vc1 of the capacitor C1 is expressed by the following equation.

$$Vc1 = VDD \times (Cs1 + Cs2)/C1 \quad (7)$$

Since the output voltage Vo of the amplifier circuit OP1 is higher than the voltage Vc1 of the capacitor C1 by the reference voltage Vref, the output voltage Vo of the amplifier circuit OP1 is expressed by the following equation.

$$Vo = VDD \times (Cs1 + Cs2)/C1 + Vref \quad (8)$$

As shown in equation (8), the voltage Vo output from the amplifier circuit OP1 in the first stage of the inspection sequence is a voltage higher than the reference voltage Vref. Assuming that each of the capacitors Cs1, Cs2, and C1 generally has a fixed value, the output voltage Vo shown in equation (8) also generally has a fixed value. In particular, when the output voltage Vo expressed in equation (8) exceeds the power supply voltage VDD, the output voltage Vo becomes a value close to the power supply voltage VDD.

FIGS. 5A to 5D are diagrams for explaining the state of the switching circuit and the voltage of each portion in the first stage of the inspection sequence, and show a case where there is no breakage of the signal line. As shown in FIG. 5D, the output voltage Vo when there is no breakage of the signal line is a value higher than a predetermined threshold voltage Vth1.

Figure 6:
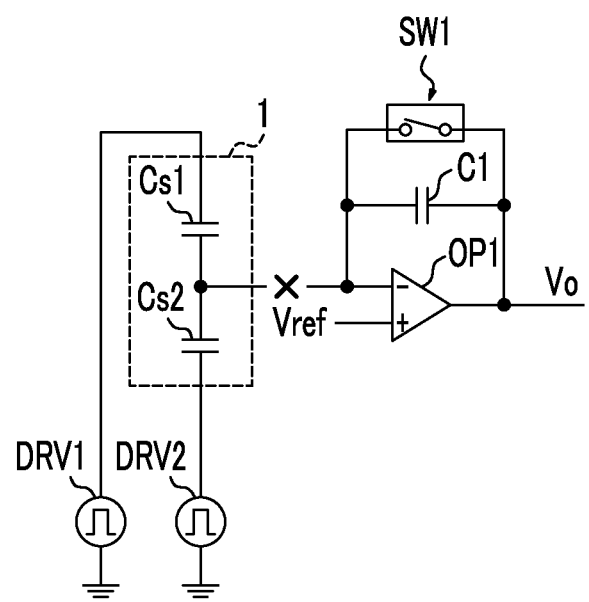
FIG. 6 is a diagram showing a case where the signal line of the sensor device is broken.

However, if the signal line connecting the signal terminal T3 of the sensor unit 1 and one end of the capacitor C1 to each other is broken as shown in FIG. 6, even if the switching circuit SW1 is turned off during the charge transfer period Tchg, electric charges from the sensor unit 1 are not transferred to the one end of the capacitor C1. Accordingly, no electric charge is accumulated in the capacitor C1.

FIGS. 7A to 7D are diagrams for explaining the state of the switching circuit and the voltage of each portion in the first stage of the inspection sequence, and show a case where the signal line is broken. When the signal line is broken, the output voltage Vo in the charge transfer period Tchg hardly changes compared with the reset period Trst. Accordingly, the output voltage Vo remains at the reference voltage Vref. The output voltage Vo in this case is an abnormal value that is certainly lower than the threshold voltage Vth1.

Therefore, the control circuit 2 compares the voltage Vo, which is output from the amplifier circuit OP1 in the charge transfer period Tchg of the first stage, with the threshold voltage Vth1, and determines whether or not the output voltage Vo is included in a normal range that is higher than the threshold voltage Vth1 (ST20). For example, the control circuit 2 performs this determination by comparing the detection data Ds generated by the AD conversion circuit 3 with data of the threshold voltage Vth1 set in the register or the like in advance. When the output voltage Vo is included in the normal range, the control circuit 2 proceeds to the next second stage (ST30, ST35, and ST40). When the output voltage Vo is not included in the normal range, the control circuit 2 writes a predetermined determination value indicating that there is an abnormality, such as breakage, in the signal line in the register 4 (ST25), and ends the inspection. Second Stage (ST30, ST35, ST40)

Figure 8A:
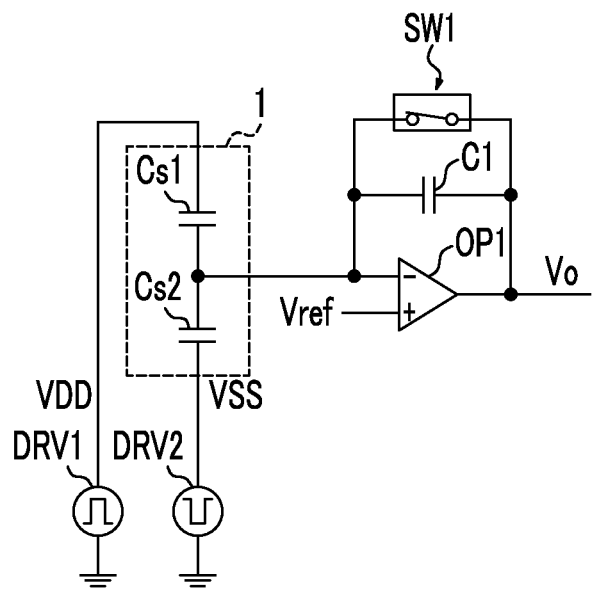
FIGS. 8A and 8B are diagrams showing the operating state of the sensor device in a second stage of the inspection sequence, where
Figure 8B:
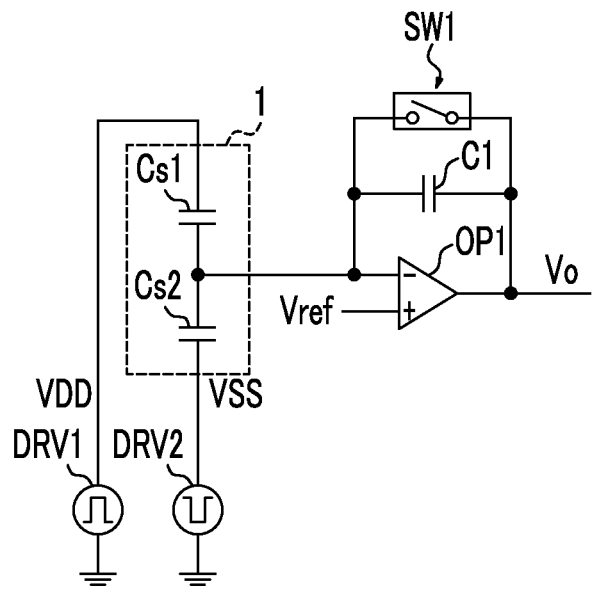

In the reset period Trst of the second stage, the control circuit 2 turns on the switching circuit SW1 to discharge the electric charges of the capacitor C1, and outputs the high-level driving voltage VDD from the first driving circuit DRV1 and outputs the low-level driving voltage VSS from the second driving circuit DRV2 (ST30). FIG. 8A shows the operating state of the sensor device in the reset period Trst of the second stage.

Then, in the charge transfer period Tchg of the second stage, the control circuit 2 turns off the switching circuit SW1 so that the capacitor C1 can be charged (discharge of the capacitor C1 is released), and outputs the low-level driving voltage VSS from the first driving circuit DRV1 and outputs the high-level driving voltage VDD from the second driving circuit DRV2.

The operation in the reset period Trst and the charge transfer period Tchg in the second stage is the same as the normal measurement sequence previously described. Therefore, as shown in equation (4), the voltage Vo output from the amplifier circuit OP1 in the charge transfer period Tchg of the second stage is proportional to a difference Cs1−Cs2 between the capacitance of the first capacitive sensor element Cs1 and the capacitance of the second capacitive sensor element Cs2.

FIGS. 9A to 9D are diagrams for explaining the state of a switching circuit and the voltage of each portion in the second stage of the inspection sequence, and show a normal case where there is no breakage or the like. As shown in FIG. 9D, the output voltage Vo in the normal state is included in a predetermined normal range (range from a threshold voltage Vth2 to a threshold voltage Vth3) including the reference voltage Vref.

Figure 10:
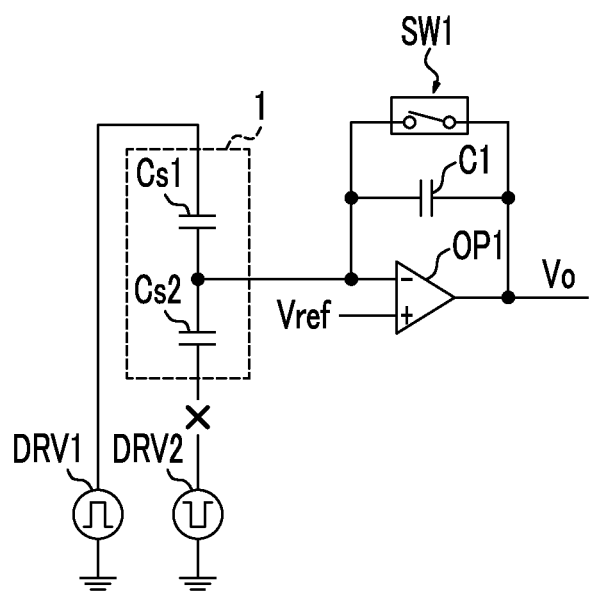
FIG. 10 is a diagram showing a case where the wiring line of a driving circuit of a sensor device is broken.

Incidentally, when one of the wiring lines connecting the sensor unit 1 and the driving circuits DRV1 and DRV2 to each other is broken as shown in FIG. 10, the input and output of electric charges in a capacitive sensor element connected to the broken wiring line do not occur. Accordingly, the capacitance of the capacitive sensor element can be regarded as zero equivalently. That is, "Cs1" or "Cs2" in equation (4) is zero. Therefore, the output voltage Vo becomes an abnormal value that is not included in the normal range (range from the threshold voltage Vth2 to the threshold voltage Vth3).

FIGS. 11A to 11D are diagrams for explaining the state of a switching circuit and the voltage of each portion in the second stage of the inspection sequence, and show a case where the wiring line of the second driving circuit DRV2 is broken as shown in FIG. 10. As shown in FIG. 11D, the output voltage Vo in this case is an abnormal value higher than the threshold voltage Vth3 of the upper limit of the normal range.

Figure 12A:
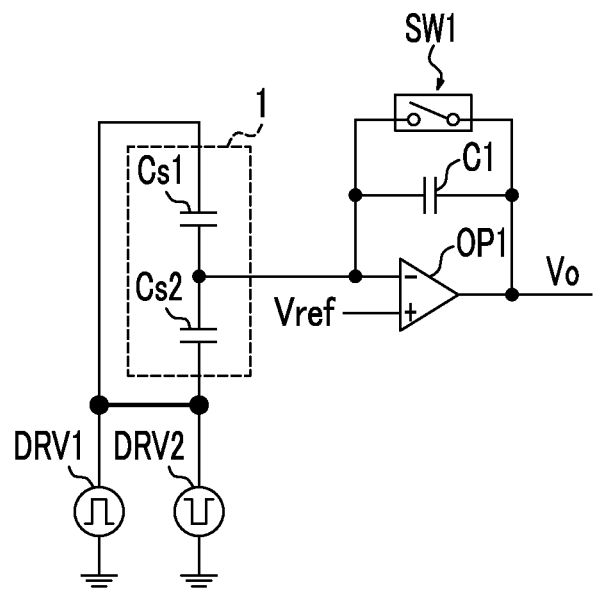
FIGS. 12A and 12B are diagrams showing other abnormal states inspected in the second stage of the inspection sequence, where
Figure 12B:
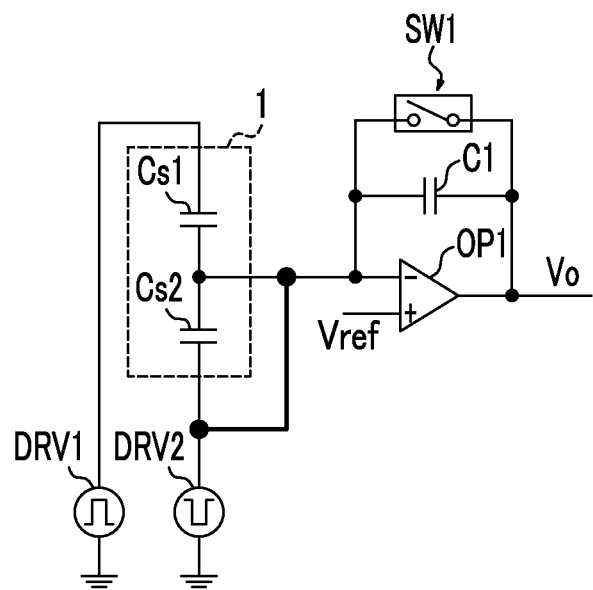

FIGS. 12A and 12B are diagrams showing other abnormal states inspected in the second stage of the inspection sequence. FIG. 12A shows a case where the wiring lines of the first and second driving circuits DRV1 and DRV2 are short-circuited, and FIG. 12B shows a case where the wiring line of the second driving circuit DRV2 and the signal line are short-circuited. The case where the wiring lines of the two driving circuits are short-circuited as shown in FIG. 12A is substantially the same as the case where the sensor unit 1 is driven by the voltages having the same phase as in the first stage that has been previously described. Accordingly, the output voltage Vo of the amplifier circuit OP1 becomes an abnormal value close to the power supply voltage VDD side or the ground potential VSS side. Also when the wiring line of a driving circuit and the signal line are short-circuited as shown in FIG. 12B, the output voltage Vo becomes an abnormal value deviating from the normal range.

Therefore, the control circuit 2 compares the voltage Vo, which is output from the amplifier circuit OP1 in the charge transfer period Tchg of the second stage, with the threshold voltages Vth2 and Vth3, and determines whether or not the output voltage Vo is included in a normal range from the threshold voltage Vth2 to the threshold voltage Vth3 (ST40). For example, the control circuit 2 performs this determination by comparing the detection data Ds generated by the AD conversion circuit 3 with data of the threshold voltages Vth2 and Vth3 set in the register or the like in advance. When the output voltage Vo is included in the normal range, the control circuit 2 writes a predetermined determination value indicating that there is no abnormality, such as breakage or short-circuiting, in the register 4 (ST50). On the other hand, when the output voltage Vo is not included in the normal range, the control circuit 2 writes a predetermined determination value indicating that there is an abnormality, such as breakage or short-circuiting, in the wiring line of the driving circuit in the register 4 (ST45).

As described above, according to the inspection method of the sensor device of the present embodiment, the capacitor C1 is discharged by the switching circuit SW1 and the high-level driving voltage VDD is output from both of the first and second driving circuits DRV1 and DRV2 in the reset period Trst of the first stage, and the discharge of the capacitor C1 by the switching circuit SW1 is released and the low-level driving voltage VSS is output from both of the first and second driving circuits DRV1 and DRV2 in the charge transfer period Tchg subsequent to the reset period Trst. Then, it is determined whether or not the output voltage Vo of the amplifier circuit OP1 in the charge transfer period Tchg is included in a predetermined normal range, and a determination result indicating an abnormal state, such as the breakage of the signal line, is obtained when the output voltage Vo of the amplifier circuit OP1 is not included in the normal range. Therefore, it is possible to accurately check the abnormality, such as the breakage of the signal line, without affecting the normal capacitance measurement while realizing a sensor device using a capacitive sensor element.

In addition, according to the inspection method of the sensor device of the present embodiment, when it is determined that the output voltage Vo in the first stage is included in the normal range, the capacitor C1 is discharged by the switching circuit SW1 and the high-level driving voltage VDD is output from the first driving circuit DRV1 and the low-level driving voltage VSS is output from the second driving circuit DRV2 in the reset period Trst of the second stage, and the discharge of the capacitor C1 by the switching circuit SW1 is released and the low-level driving voltage VSS is output from the first driving circuit DRV1 and the high-level driving voltage VDD is output from the second driving circuit DRV2 in the charge transfer period Tchg subsequent to the reset period Trst. Then, it is determined whether or not the output voltage Vo of the amplifier circuit OP1 in the charge transfer period Tchg is included in a predetermined normal range, and a determination result indicating an abnormal state, such as the breakage or short-circuiting of wiring lines of driving circuits, is obtained when the output voltage Vo of the amplifier circuit OP1 is not included in the normal range. Therefore, an abnormal state, such as the breakage or short-circuiting of wiring lines of driving circuits can also be accurately inspected.

While one embodiment of the present invention has been described above, the present invention is not limited to the above embodiment, and includes various variations.

Figure 13:
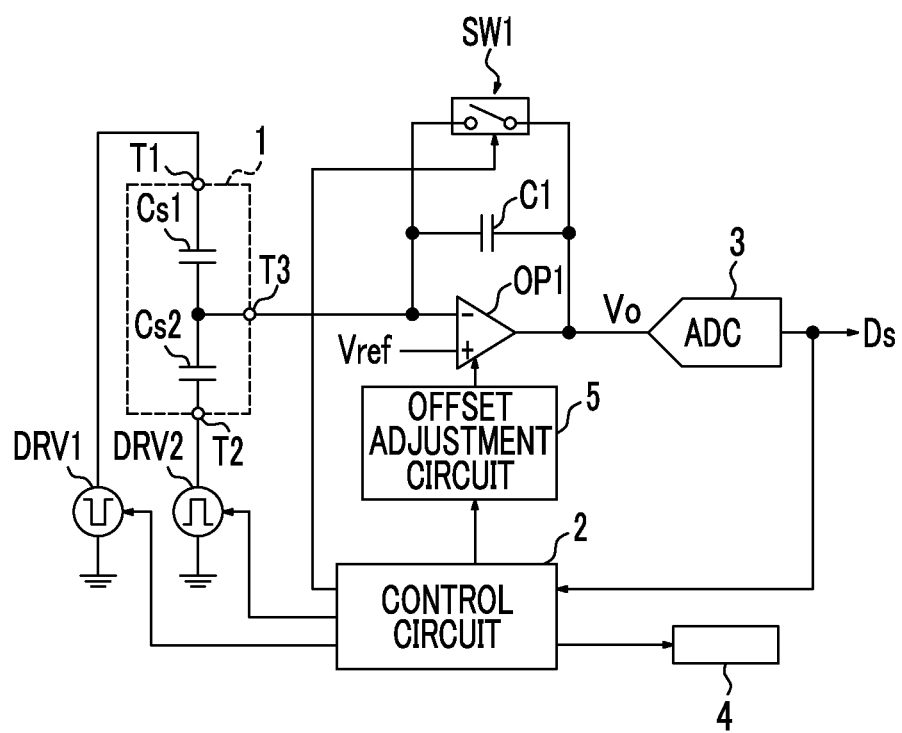
FIG. 13 is a diagram showing another example of the sensor device according to the present embodiment.
Figure 14A:
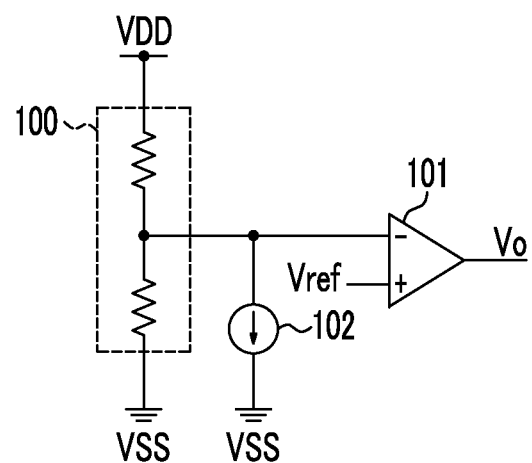
FIGS. 14A and 14B are diagrams showing the configuration of a resistive humidity sensor, where
Figure 14B:
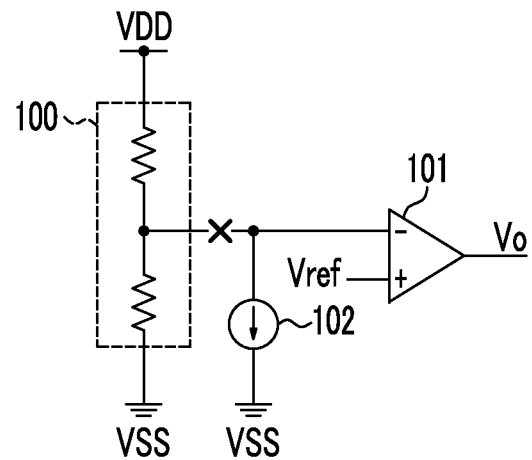
Figure 15:
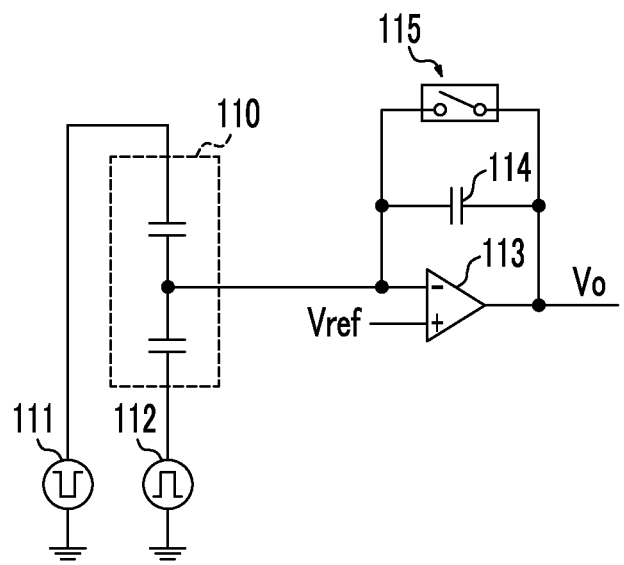
FIG. 15 is a diagram showing the configuration of a capacitive humidity sensor.

FIG. 13 is a diagram showing another example of the sensor device according to the present embodiment, and shows an example in which an offset adjustment circuit 5 for adjusting an offset voltage appearing at the output of the amplifier circuit OP1 according to the charge signal of the sensor unit 1 or the like is provided. When the inspection of the first stage is performed in a state where the adjustment of the offset voltage by the offset adjustment circuit 5 is enabled, erroneous determination that there is no abnormality may be performed even though there is an abnormality, such as the breakage of the signal line, because the output voltage Vo exceeds the threshold voltage Vth1 due to the offset voltage being added. For this reason, when the offset adjustment circuit 5 is provided, the control circuit 2 disables the adjustment of the offset voltage by the offset adjustment circuit 5 in the inspection (steps ST10 and ST15 in FIG. 3) of the first stage, and enables the offset voltage adjustment function in the inspection (steps ST30 and ST35 in FIG. 3) of the second stage. Therefore, it is possible to effectively prevent erroneous determination in the first stage. In addition, also in the second stage, it is possible to perform an accurate determination since the output voltage Vo is easily included in the normal range in the normal state.

In the explanation of the first stage described above, the driving voltage in the reset period Trst is set to the high level and the driving voltage in the charge transfer period Tchg is set to the low level. However, this is just an example, and the driving voltage in the reset period Trst may be set to the low level and the driving voltage in the charge transfer period Tchg may be set to the high level in another embodiment of the present invention.

In the embodiment described above, an example has been mentioned in which one reset period Trst and one charge transfer period Tchg are set in the first stage or the second stage of the inspection sequence. However, the present invention is not limited thereto. In another embodiment of the present invention, a plurality of reset periods Trst and a plurality of charge transfer periods Tchg may be alternately repeated. In this case, it may be determined whether or not the integrated value or the average value of the detection data Ds obtained every charge transfer period Tchg is included in a predetermined normal range.

It should be understood by those skilled in the art that various modifications, combinations, sub-combinations and alterations may occur depending on design requirements and other factors insofar as they are within the scope of the appended claims of the equivalents thereof.

What is claimed is:

1. An inspection method of a sensor device including: a sensor unit having a first capacitive sensor element connected between a first driving terminal and a signal terminal and a second capacitive sensor element connected between a second driving terminal and the signal terminal; a first driving circuit configured to output a first driving voltage or a second driving voltage to the first driving terminal; a second driving circuit configured to output the first driving voltage or the second driving voltage to the second driving terminal; a capacitor having a first end connected to the signal terminal and a second end; an amplifier circuit configured to output an amplified voltage to the second end of the capacitor by amplifying a difference between a voltage of the signal terminal and a reference voltage such that the voltage of the signal terminal becomes close to the reference voltage; and a switching circuit configured to discharge electric charges accumulated in the capacitor, the inspection method comprising:
a first inspection stage including:
 a first step of discharging the capacitor using the switching circuit, and applying the first driving voltage to the first and second driving terminals using the first and second driving circuits, respectively;
 a second step of stopping the discharging of the capacitor using the switching circuit to make the capacitor available for charging, applying the second driving voltage to the first and second driving terminals using the first and second driving circuits, respectively, and outputting the amplified voltage by amplifying the difference between the voltage of the signal terminal and the reference voltage using the amplifier circuit; and
 a third step of determining whether or not the amplified voltage output from the amplifier circuit in the second step is within a first normal range between a first threshold voltage and a power supply voltage, the first threshold voltage being higher than the reference voltage and lower than the power supply voltage.

2. The inspection method of a sensor device according to claim 1, further comprising:
a second inspection step including:
 a fourth step of discharging the capacitor using the switching circuit, and applying the first driving voltage to the first driving terminal using the first driving circuit and the second driving voltage to the second driving terminal using the second driving circuit;
 a fifth step of stopping the discharging of the capacitor using the switching circuit, and outputting the second driving voltage to the first driving terminal using the first driving circuit and the first driving voltage to the second driving terminal using the second driving circuit, and outputting the amplified voltage by amplifying the difference between the voltage of the signal terminal and the reference voltage using the amplifier circuit; and
 a sixth step of determining whether or not the amplified voltage output from the amplifier circuit in the fifth step is within a second normal range between a second threshold voltage and a third threshold voltage, the second threshold voltage being higher than a ground potential and lower than the reference voltage, and the third threshold voltage being higher than the reference voltage and lower than the power supply voltage,
wherein the second inspection stage is performed if the first inspection stage determines that the amplified voltage output from the amplifier circuit is within the first normal range.

3. The inspection method of a sensor device according to claim 2,
wherein the sensor device includes an offset adjustment circuit configured to adjust an offset voltage of the amplifier circuit,
and wherein a function of the offset adjustment circuit is disabled in the first inspection stage and enabled in the second inspection stage.

4. A sensor device, comprising:
a sensor unit including:
 a first capacitive sensor element connected between a first driving terminal and a signal terminal; and
 a second capacitive sensor element connected between a second driving terminal and the signal terminal;
a first driving circuit configured to output a first driving voltage or a second driving voltage to the first driving terminal;

a second driving circuit configured to output the first driving voltage or the second driving voltage to the second driving terminal;

a capacitor having a first end connected to the signal terminal and a second end;

an amplifier circuit configured to output an amplified voltage to the second end of the capacitor, by amplifying a difference between a voltage of the signal terminal and a reference voltage, such that the voltage of the signal terminal becomes close to the reference voltage;

a switching circuit configured to discharge electric charges accumulated in the capacitor; and a control circuit configured to control the first driving circuit, the second driving circuit, and the switching circuit such that the amplified voltage output from the amplifier circuit corresponds to a difference between a capacitance of the first capacitive sensor element and a capacitance of the second capacitive sensor element, wherein the control circuit is further configured to perform a first inspection stage in which the control circuit:

controls, in a first step, the switching circuit to discharge the capacitor, and both of the first and second driving circuits to output to the first driving voltage to the first and second driving terminals, respectively;

controls, in a second step, the switching circuit to stop the discharge of the capacitor to make the capacitor available for charging, and both of the first and second driving circuits to output the second driving voltage to the first and second driving terminals, respectively; and determines, in a third step, whether or not the amplified voltage output from the amplifier circuit in the second step is within a first normal range between a first threshold voltage and a power supply voltage, wherein the first threshold voltage is higher than the reference voltage and lower than the power supply voltage.

5. The sensor device according to claim 4, wherein the control circuit is further configured to perform a second inspection stage in which the control circuit:

controls, in a fourth step, the switching circuit to discharge the capacitor, the first driving circuit to output the first driving voltage to the first driving terminal, and the second driving circuit to output the second driving voltage to the second driving terminal;

controls, in a fifth step, the switching circuit to stop the discharge of the capacitor to make the capacitor available for charging, the first driving circuit to output the second driving voltage to from the first driving terminal, and the second driving circuit to output the first driving voltage to the second driving terminal; and determines, in a sixth step, whether or not the amplified voltage output from the amplifier circuit in the fifth step is within a second normal range between a second threshold voltage and a third threshold voltage, the second threshold voltage being higher than a ground potential and lower than the reference voltage, and the third threshold voltage being higher than the reference voltage and lower than the power supply voltage, and wherein the second inspection stage is performed if the control circuit determines that the amplified voltage output from the amplifier circuit in the first inspection stage is within the first normal range.

6. The sensor device according to claim 5, further comprising:

an offset adjustment circuit configured to adjust an offset voltage of the amplifier circuit, wherein the control circuit disables a function of the offset adjustment circuit in the first inspection stage, and enables the function the offset adjustment circuit in the second inspection stage.

* * * * *